United States Patent
Nesveda

(10) Patent No.: US 12,202,779 B2
(45) Date of Patent: Jan. 21, 2025

(54) METHOD FOR PRODUCING ECOLOGICAL EXPLOSIVE FOR PRIMER COMPOSITIONS OF AMMUNITION

(71) Applicant: SELLIER & BELLOT A.S., Vlasim (CZ)

(72) Inventor: Jiri Nesveda, Vlasim (CZ)

( * ) Notice: Subject to any disclaimer, the term of this patent is extended or adjusted under 35 U.S.C. 154(b) by 1024 days.

(21) Appl. No.: 17/265,890

(22) PCT Filed: Aug. 8, 2019

(86) PCT No.: PCT/CZ2019/000038
§ 371 (c)(1),
(2) Date: Feb. 4, 2021

(87) PCT Pub. No.: WO2020/030203
PCT Pub. Date: Feb. 13, 2020

(65) Prior Publication Data
US 2021/0163376 A1    Jun. 3, 2021

(30) Foreign Application Priority Data

Aug. 8, 2018  (CZ) ............................. PV 2018-408

(51) Int. Cl.
| | | |
|---|---|---|
| C06B 43/00 | (2006.01) | |
| C06B 27/00 | (2006.01) | |
| C06B 31/02 | (2006.01) | |
| C07D 257/06 | (2006.01) | |
| C07F 9/94 | (2006.01) | |

(52) U.S. Cl.
CPC .............. *C06B 43/00* (2013.01); *C06B 27/00* (2013.01); *C06B 31/02* (2013.01); *C07D 257/06* (2013.01); *C07F 9/94* (2013.01)

(58) Field of Classification Search
None
See application file for complete search history.

(56) References Cited

U.S. PATENT DOCUMENTS

| | | | |
|---|---|---|---|
| 5,939,045 A | 8/1999 | Suzuki et al. | |
| 2016/0280614 A1* | 9/2016 | Nesveda | .................. C06C 7/00 |

FOREIGN PATENT DOCUMENTS

| | | |
|---|---|---|
| CN | 106045929 A | 10/2016 |
| CZ | 305 403 U1 | 2/1993 |
| DE | 10 2010 036 950 A1 | 8/2010 |

OTHER PUBLICATIONS

ISR; European Patent Office; NL; Jun. 11, 2019.
ISR; Industrial Property Office of the Czech Republic; May 27, 2019.
Synthesis PF 5-Aminotetrazole-1 N-Oxide and Its AZO Derivative: a Key Step in the Development of New Energetic Materials; Fischer et al; 2013.
Synthesis of Insensitive 5, 5W- Azotetrazolate Salts; Journal of Energetic Materials; 2011.
Hydrazinium 5- Aminotetrazolate; an Insenssitive Energetic Material Containing 83.72% Nitrogen; 2008.
Anton Hammerl et al; "Salts of 5, 5—Azotetrazolate" Mar. 1, 2002.

* cited by examiner

*Primary Examiner* — Aileen B Felton
(74) *Attorney, Agent, or Firm* — Patshegen IP; Moshe Pinchas

(57) ABSTRACT

The invention discloses a method for producing ecological primary explosive—basic bismuth(III) salt of 5,5'-bis-azotetrazole and its using in ecological mixture for primer compositions of ammunition.

4 Claims, No Drawings

METHOD FOR PRODUCING ECOLOGICAL EXPLOSIVE FOR PRIMER COMPOSITIONS OF AMMUNITION

FIELD OF THE INVENTION

The invention relates to a new ecological explosive, suitable for primer compositions of ammunition, and a method of its production.

BACKGROUND ART

In 2013, the firm Sellier & Bellot a.s., as one of the largest European producers of ammunition, filed an application of invention No. PV 2013-858 in the Czech Republic on which a patent CZ 305 403 relating to energetic compounds based on bismuth has been granted. It describes laboratory preparation as well as physical, chemical, and particularly fundamental explosive properties of new, so far non-described compounds which are basic salts of trivalent Bi with anions of known energetic compounds. The described compounds can have various industrial utilization depending on their explosive and physico-chemical properties—for using in ammunition primers (as so-called main initiating explosives); however, compounds of specific properties should be chosen—in which way, these initiating explosives principally differ from other explosives usable e.g. in detonators, electric fuses or squibs in airbags.

Primary explosives to central and rimfire ammunition must be able to burn stably (i.e. having sufficiently long pre-detonation zone) and rate of burning must be as little as possible dependent on external pressure in a wide pressure range—this property is typical of so-far for this purpose irreplaceable lead trinitroresorcinate which is unfortunately absolutely inconvenient from the current ecological point of view. In this way, it is ensured that deflagration of initiating explosive in a primer composition will not change to detonation, which must not be the case—in detonators, the requirement is completely opposite and the most suitable initiating explosive for detonators cannot burn at all.

Further specific requirement is sensitivity to stab ignition, which is a special method of primer initiation—by stroke onto a very small area (with stab-ignition needle, anvil in central fire amunition, or stroke onto a small area of cartridge rim—at rim fire ammunition). In this method of primer initiation—friction surprisingly prevails over impact, the more the sharper is the firing pin, needle or vortex angle of the anvil.

Long-term investigation and testing of many compounds has resulted in finding that even initiating explosives that neither show sufficient sensitivity to friction—i.e. those showing lower sensitivity to friction than specified 10 N (i.e. 1 kg load of porcelain pestle) nor sufficient sensitivity to impact on a Kast's apparatus—i.e. higher than 4 J (i.e. downfall of 400 g weight from the height of one metre)—can have (using suitable sensibilizers)—excellent sensitivity to stab ignition. Provided the compound has these properties—it is a highly safe compound from the handling point of view, which is one of basic criteria of applicability in the mass production.

Naturally, further criteria are resistance to electro static discharge, chemical stability—i.e. non-reactivity with common atmospheric gases, perfect compatibility with all materials used in the production of ammunition as well as with materials used in the production of primer compositions, non-hygroscopicity, and newly also so-called hydrolytic stability—resistance to hot (boiling) water and thermal stability, currently tested exclusively by DTA (differential thermal analysis) method—i.e. the method of so-called "thermal explosion". The above mentioned criteria are common for all types of industrial initiating explosives—however, the criterion of thermal stability can considerably differ depending on using of the explosive.

Explosives for primers are the only to show certain minimum, specified sensitivity to mechanical impulses (to the above mentioned stab ignition)—this is naturally directly associated with energy of the firing pin of weapons which is not unlimited and is strictly defined according to the type of a weapon. During the stroke (stab ignition), kinetic energy of the firing pin degrades to thermal energy and the subsequently released amount of heat must be sufficient for the local increasing of temperature to be higher than temperature of explosion point of the initiating explosive in the composition. Therefore, explosives with high explosion point, such as lead trinitroresorcinate (hereinafter TNRO—e.p.—270° C.), can no more do without so-called active sensitizers—auxiliary initiating explosives, such as, in this case, tetrazene (explosion point 130-140° C.) which is, in the amount of 3-5%, able to subsequently initiate also LeadTNR by the heat liberated in the exothermic reaction itself. Here, a paradox appears—tetrazene which is, thanks to its low explosion point, an irreplaceable "auxiliary" initiating explosive in the case of using highly thermal stable initiating explosives, such as LeadTNR, is currently designated as thermally instable and, therefore, unsuitable for modern primer compositions, but, on the other hand, using of highly termal-stable initiating explosives in primer caps is problematic without it.

Thus, the solution must be a compromise—explosion point of the explosive must be high enough so that the explosive would be still considered thermally stable, but not so high that it would require using active sensitizers of the type of tetrazene. Experience has shown that optimum temperature of explosion point of the primary explosives for primers ranges between 160 and 200° C., and, provided they show sufficient sensitivity to stab ignition, using of active sensitizers is not necessary. Another situation arises in using highly termal-stable initiating explosives in detonators (e.g. for works in underground mines or for releasing heads of boring machines from depths of several kilometres) or in airbags installed close to combustion engines under permanent thermal stress of high temperatures (see published US Patent Application No. 20080308201 with the title: "Heat-stable combustible matter based on binary calcium-potassium styphnate" with explosion point above 350° C.).

The above mentioned criteria of selecting suitable initiating explosive for primers should be completed with ability of heat transfer from the composition to propellant charge. It is desirable, that not only pyrotechnic system of the primer composition but also the initiating explosive itself contribute to ignition impulse, not only with gases of high temperature T but also with further mechanism of heat transfer, e.g. by generating condensed products of higher order thermal capacity (solid and liquid products), or phase transition, i.e. condensation of metal vapours of a low-boiling metal bound in the compound molecule, which is fulfilled in the case of Bi salts. Naturally, into considerations must also be taken complexity and expensiveness of the reaction, availability of starting products, but also ecology of the production process itself (e.g. potassium salts of 2,4-dinitrobenzo furoxane would be one of the so-called ecological substitutes of contemporary initiating explosives—however, it's production is based on insofar toxic raw materials—confirmed carcinogens, such as picryl chloride or o-nitroaniline, and environmental pollution during production is so serious that even these compounds cannot be considered as so-called "green" initiating explosives, not to speak of high sensitivity to electrostatic discharge and strongly corrosive explosive products).

After thorough consideration of all the above mentioned fact, selection has been made of basic Bi salts of 5,5 azotetrazole. 5,5 azotetrazole, in the form of pentahydrate of disodium salt, discovered as early as in the end of the 19th century by the German chemist J. Thiele, is one of perspective explosive tetrazole derivatives that, after more than 100 years, is coming into focus of experts in the field of new energetic materials.

Its production, i.e. by a simple and single-stage reduction of currently commercially available 5-aminotetrazole, is one of the simplest methods of producing explosion tetrazoles; pentahydrate of its disodium salt produced by this reaction is an ideal precursor in production of further tetrazole derivatives and salts. Five molecules of water of crystallization bound in its molecule makes this compound absolutely safe for handling and storage, and after wetting with 25% of water, also safe in usual transportation. Salts of heavy and noble metals, known as early as in the 19th century, are highly sensitive to mechanical impulses (mainly Ag and Cu salts) and, therefore, they are classified as "hazardous for handling". On contrary, some basic salts (e.g. basic salt of Pb) have come to practical using in the past (during the II w. war, its production for electric fuses was initialized in Germany). From all explosive derivatives of 5-substituted tetrazoles—it is 5,5'-azotetrazole that forms the most insoluble salts—both salts of metals and salts of organic bases. Thus, these salts can be prepared by simple metathesis, i.e. by pouring two reaction solutions together— wherein the required salt precipitates from the solution with a sufficient yield. In case of other tetrazole derivatives (e.g. 5-nitrotetrazole), some salts (particularly salts of organic bases, such as guanidine and its derivatives) cannot be prepared by this method and much more complicated reaction procedures must be applied (displacement of free tetrazole from soluble salts by means of ion-exchangers and reaction of formed free tetrazole with particular organic base, and necessary isolation of the product by concentration of the reaction solution in a vacuum evaporator). Therefore, the insoluble salts of 5,5'-azotetrazole with guanidine and its amino derivatives (amino-, diamino- and triamino-guanidine) belong among the most desired highly nitrogenous energetic materials for gas generators, rocket propellants, and, mainly, airbags.

Pentahydrate of disodium salt of 5,5-azotetrazole is not commercially available (it is not offered in any catalogue of chemicals) but it is usually produced by some factories as a intermedial-product in producing the above mentioned salts. In the Czech Republic, it is produced by VUPCH Explosia Semtín, from which it will be also taken by the firm Sellier & Bellot, a.s., following a mutual agreement. Final product of this production is the salt of guanidine under the trade designation GZT (bis-guanidinium azotetrazolate).

However, 5,5'-azotetrazole differs, with its chemical properties, from other explosive tetrazole derivatives. The more stable are its salts, the more unstable it is itself, in the form of free acid, displaced from its salts with mineral acids. Final products of this decomposition reaction, i.e.—from 1 mole of 5,5-azotetrazole are −2 moles of gaseous nitrogen are generated (by decomposition of one tetrazole ring), one mole of 5-hydrazotetrazole and one mole of formic acid. However, the course of reaction is more complex; under certain conditions (using of excess of cold oxidizing acids or using of just exactly calculated amount of acid, necessary for displacement from its salt), a reaction intermedial product is also formed the composition of which is not exactly known to this day; Thiele defined this product as polymeric nitrile of 5-hydrazotetrazole. This brown amorphous product shows considerable explosive properties and both this product and by additional oxidization with water thereof formed high unstable 5-hydrazotetrazole can bind both the anion of particular acid and the cation of present metal (the molecule has basic and acidic parts). In the case of precipitation carried out in an acidic medium and using oxo-perchlorates of Bi, as described in the laboratory preparation of basic azotetrazolate of Bi in the above mentioned application of invention PV 2013-858 with the title: "Energetic materials based on Bi", complex Bi salt of perchlorate of 5-hydrazotetrazole can be formed the presence of which can negatively influence explosive properties of the final product.

Therefore, in the course of subsequent development, the mentioned method has been further modified. Due to the fact that the rate of decomposition in an acidic medium, which is necessary for precipitation of Bi salts, is extremely dependent on the temperature T, the precipitation was performed in two steps; in the first step, cold precipitation took place; then, the formed precipitate was refined by multistage decantation (in order to reduce the content of perchlorates to a minimum) and the residual product was boiled, in which way possible Bi hydrolyzates that can still contaminate the product were stabilized. Consequently, however, the method became considerably complicated; therefore, during further development, the reaction was made substantially more efficient, particularly concerning saving of quite expensive and mainly in various aspects unsafe perchloric acid, and product losses (by decomposition in an acidic medium) were substantially reduced. In the preparation of Bi perchlorate by the reaction of $Bi_2O_3$ with azeotropic perchloric acid, just one-third amount of perchloric acid (corresponding to the reaction of one Bi atom with one mole of perchloric acid) was used; in this way bismuth(III) oxide perchlorate (oxo-perchlorate) of the formula $BiOClO_4$ was directly formed and it was not gradually formed by hydrolysis of normal salt with formation of 2 moles of perchloric acid which would make the reaction mixture extremely acidic. Then, precipitation was carried out at pH ranging between 2 and 3; the losses by decomposition were thus limited to a minimum and the content of perchlorates was also reduced. The yield increased to a double, however, performance of the resulting product was reduced by about 20% and, in the DTA test, no explosion but only exothermic reacting occurred, as documented by a small exothermic peak. However, this product was highly chemically stable and non-hygroscopic. When put on a free area and exposed to day sunlight, it considerably changed its colour (from canary yellow or yellow-green) to grey or grey-brown tint within several days. The phenomenon was only detected on the surface without a least effect on explosive properties, however, according to current very strict criteria, this could be evaluated as a demonstration of instability. This is a photocatalytic effect to which some compounds of Bi are very liable. By the action of visible and UV radiation, water (from atmospheric humidity) is decomposed with formation of oxygen radicals that can oxidize e.g. some functional groups of organic substances (azo groups). However, this depends on the used anion to which Bi is linked. Moreover, anions of strongly oxidizing acids, such as the perchlorate, can oxidize elements with changeable valence (such as just Bi) and, as it is well known, some higher oxides of Bi are markedly coloured.

Apart from all the above mentioned drawbacks of the method used, the main problem proved to be using of the perchloric acid itself. On one hand, using of perchloric acid proved to be optimum and oxo-perchlorates of Bi belong among the best donors of Bi for precipitating reactions in an aqueous medium, which is generally given by solubility of perchlorates (inorganic as well as organic), effect of wake bond of the huge perchlorate anion with just one valence electron with cations. The using of perchloric acid, particularly in the mass production, is highly problematic (not to speak of its price). This is an acid with extreme oxidizing properties the thermal and chemical stability of which decreases considerably with increasing concentration. In the form of the azeotrope (70-72%), it is generally commercially available, but it is only supplied in 1-litre bottles and must be very pure (mainly free of the least traces of organic substances that could lead to exothermic reactions and subsequent inflammation or even explosion)! During handling, even in a laboratory, strict safety measures must be followed and only highly professionally qualified persons can work with it. In particular, it must not come into contact with any reduction agents (this also concerns some metals) or with organic substances (this also concerns common materials, such as e.g. wood or dressing textiles); workers must be provided with special protective equipment. The most strict safety measures apply to work at elevated temperatures—above 150° C., when vapours of perchloric acid can be generated. Here, it is necessary to use special exhaust hoods—designed exclusively for work with this acid where no other chemicals must be used. During the work or storage, concentration must not exceed the azeotrope (i.e. above 72-73%)! Such acid is already thermally instable and, under unsuitable storage conditions, spontaneous decomposition can take place, which often ends with explosion! The above-azeotropic and, in particular, anhydrous perchloric acid is considered dangerous and highly unstable explosive (it can explode even during pouring from a bottle). In the mass production, the requirements for safety are naturally considerably higher. However, not only the perchloric acid itself but generally the perchlorate anion—represents even further serious problem, namely its removing from waste water. The investigations carried out since the 90th have proved that the perchlorate anion blocks function of the thyroid and thus it has an extremely negative effect on development of human foetus—teratogenic effects (apart from high toxicity for aquatic organisms). Therefore, newly specified limits for the content of perchlorates in waters are extremely low (about 25 ppb in drinking water).

Treatment of waste water containing perchlorates is a very difficult task and no such technology is known in the Czech Republic (firms engaged in delaboration of rocket SP, based on ammonium perchlorate employ the so-called closed process—perchlorates are just recycled). The greatest problem is extreme chemical resistance of the perchlorate anion. Contrary to similar large anions of oxidizing acids, this anion is extremely resistant to action of common reduction agents (sulphides, thiosulphates, dithionites (hyposulphites) etc.) and the reduction takes place only in a medium with extreme acidity (acid concentration 4M and higher). Therefore, more and more efficient methods of degrading perchlorates are being developed with using bacterial or enzymatic anaerobic bio-filters (with a fluid bed) that gradually reduce the perchlorate ion to chlorate, chlorite and finally to harmless chloride. However, all these methods are still in the phase of development and, according to experts' opinions, they are only suitable for treatment of surface and ground waters; thus, for industrial waters, where concentration of perchlorates of higher order of magnitude is expected, these methods will not be sufficiently efficient.

Methods are currently arising that specifically remove e.g. only ammonium perchlorate based on entrapping the ion on hydrogels based on poly allyl amine hydrochloride etc.

Apparently, the simplest would be physical methods; e.g. using of molecular sieves by the method of reverse osmosis, which is particularly suitable for the huge perchlorate ion, or using of ion-exchange columns. However, these methods still lack final solution of the problem of further processing of perchlorate concentrates formed here as one of products.

Recently, combined methods have also been proposed, e.g. entrapping of perchlorates on an active ion-exchange membrane, etc.

In any case, these technologies are so complicated, that using of such technology in our process of producing the new explosive would mean extreme complication and huge financial expenses. According to experts' opinion, this would, in our particular case, mean even development of a new technology of waste water treatment with the outlook to many years to come.

The substitution of perchloric acid in the production process has thus proved to be of absolute priority. As an acid with similar properties does not exist, it was clear that its substitution will have to be connected with basic changes in the production process (compared with laboratory preparation disclosed in the Czech application of invention No. PV 2013-858 with the title "Energetic materials based on Bi"), and also concerning specific properties of 5,5'-bis-azotetrazole the disodium salt of which has been chosen as one of starting raw materials for this reaction.

DISCLOSURE OF THE INVENTION

All the above mentioned disadvantages of the process of laboratory preparation of basic Bi salts of 5,5'-azotetrazole resulting from the Czech application of invention No. PV 2013-858 with the title "Energetic materials based on Bi" are eliminated by the solution according to this invention, which also enables application of this process in the mass production.

The priority task has been substitution of perchloric acid and its complete elimination from the process.

In the choice of a suitable substitute, attention was focused on strong organic or inorganic acids with sufficiently large anion and only one valence electron, with as simple molecule as possible, having ability to form as soluble as possible salts with most metals, without undesirable oxidizing properties, with as low as possible vapour pressure at room temperature T (approximately 20-25° C.), and high thermal stability, non-producing toxic and harmful fumes, perfectly miscible with water and polar organic solvents, and easily bio-degradable under natural conditions.

All the above mentioned requirements are met by the simplest and commercially commonly available representative of the so-called alkane sulphonic acids—methane sulphonic acid of the formula $CH_3SO_2OH$ (hereinafter MSA—methane sulphonic acid). This is a strong organic acid (pKa=−1.92) which, concerning ability to dissociate ("strength"), stands between the strongest carboxylic acids and strong inorganic acids (it is completely dissociated in 0.1 M solution). It is liquid at temperature higher than 20° C., boils at 167° C., and, compared with nitric or perchloric acids, it is highly thermal-stable. It is extremely easy to bio-degrade, compatible with oxidizing agents, fuels as well as biocides. It is the least toxic from all known "strong"

acids and relatively most safe in handling. Thanks to these exceptionally positive properties, it is called "green acid".

It was first synthetized in 1950 by J. C. Snyder and A. V. Gross at Houdry Process Corp. by heating methane with sulphur trioxide at the temperature 200-325° C., the reaction being catalyzed with mercury salts. Firm BASF in Ludwigshafen developed a more simple method based on oxidation of dimethyl sulphide (common waste of cellulose production by sulphite method); in 2015, firm Grillo-Werke in Duisburg developed a process of producing alkane sulphonic acids by reaction of alkanes with sulphur trioxide with presence of organic peroxides at temperature 65° C. and pressure 11 MPa. Currently, firm BASF produces 30,000 tonnes per year of highly refined MSA under trade name Lutropur MSA. At present, MSA has very wide utilization, both in chemical (catalyst of polymerization, esterification, acylation, and alkylation, condenzation and cyclization reactions), and in electrochemical industries (in galvanic procedures—metal coating, Sn/Pb solders, manufacturing of printed circuits, and excellent electrolyte for some kinds of cells), but also as excellent solvent and neutralizer (dissolving of boiler scale and various deposits—e.g. in distilleries), as well as in industrial cleaning (e.g. removing of lead deposits), more and more often as a substitute for hazardous in and in water hardly degradable phosphates in many types of detergents (including household using).

MSA is a natural component and a part of the eco-system. Bio-degradation of ocean biomass (mainly seaweed) liberates dimethylsulphide (DMS), a gaseous substance responsible for the typical "sea aroma". It escapes from sea water into the atmosphere where its oxidation takes place by the action of high-energy UV radiation and oxygen radicals with formation of MSA. It returns back to the Earth surface dissolved in rain water and, by means of aerobic methylotrophic and sulphur bacteria, it degrades in the vicinity of the Earth surface to $CO_2$, sulphates and water. Naturally occurring salts of MSA dissolve in ground water—close to the surface. The bacteria controlling degradation of MSA belong to the lowest stage of food chain of the ecological system and formation of biomass is thus beginning of the natural ecological cycle. These are particularly *Escherichia coli* K-12 and *Chlorela fusca*; the most important from enzymes accelerating degradation is MSA monooxygenase.

Of course, MSA is currently also an integral part of the Bi chemistry and solutions of methane sulphonate of Bi are now commercially available in the form of about 1 M solution (relative to Bi), stabilized with several percent of free MSA. These very solutions were used in the process of preparation and later also production of basic azotetrazole of Bi (hereinafter BBA—Basic Bismuth Azotetrazolate) according to this invention. Neither MSA nor its salts have so far been used for preparation of energetic materials (i.e. in the explosives industry or pyrotechnics).

Thus, one of two basic raw materials in this process has become about 1 M (i.e. 200-210 g Bi/l) solution of methane sulphonate of Bi (MSBi) stabilized with about 3% of free MSA which is the most easily commercially available from alkane sulphonates of Bi. The using of this solution means the first considerable simplification of the process (there is no need to produce commercially unavailable bismuth(III) oxide perchlorate by the reaction of concentrated perchloric acid with $Bi_2O_3$, wherein a solid mixture of oxo-perchlorates of various solubilities is formed; it is necessary to first transfer this mixture into solution, subsequently filter off insoluble portions, fill up the solution to mark in a volumetric flask and standardize it by titration of Bi in presence of tartaric acid and after adjusting pH to 2-3 with solution K III to xylenol orange). The commercially available solution of MSBi of known Bi content should be just diluted as required, pH adjusted to an optimum value, and the solution is prepared for precipitation.

Further increase of efficiency and quality of the reaction process is based on the reaction kinetics of both "competitive" reactions that take place during precipitation of the disodium salt of azotetrazole in an acidic medium which is necessary for maximum reduction of the content of undesirable hydrolyzates of Bi: precipitation of basic Bi salt of azotetrazole that proceeds at high rate and depends mainly on concentration of Bi ions, and undesirable decomposition of azotetrazole to the above mentioned products wherein the reaction rate depends very strongly on pH of the solution and reaction temperature (T), as it was practically verified. At room temperature, in very strong acidic solutions (pH from negative values to 1) the decomposition is completed within several hours; however, at elevated temperature or even under boil, which conditions being necessary for reaching as large as possible particles of the product which is always amorphous, the decomposition is completed within several minutes and losses of the product can be as high as 60%. The precipitation at higher pH is associated with substantial reduction of losses (down to one half) but, as anticipated, also with increased content of inert hydrolyzates of Bi that deteriorate explosive properties of the final product. The resulting extremely insoluble basic azotetrazole of Bi is, as majority of basic Bi salts, incomparably(in comparison with soluble salts) more resistant (for instance, it resists without problems to action of 1 N solutions of strong acids for several days). For comparison, a test was also carried out of solubility of other insoluble compounds of Bi—$Bi_2O_3$ or $(BiO)_2CO_3$ that can be converted to sulphate by boiling in 1N solution of sulphuric acid for several hours, whereas insoluble oxides and carbonates of other common metals react under these conditions and at room temperature (T) within several minutes. Based on these findings, an idea has arisen—to change the reaction conditions and thus the course of reaction in such a way that, since the beginning of precipitation, the reaction solution would contain as high as possible concentration of Bi ions, which would maximally accelerate the precipitation of Bi azotetrazolate at the suppresion of undesirable decomposition reactions, also in a sufficiently acidic medium that ensures a minimum level of pollution with undesirable Bi hydrolysates.

A very smart solution proved to be the change of order of pouring the reaction solutions during the precipitation. In the original "perchlorate method", the saturated aqueous (about 4%) solution of disodium salt of 5,5'-bis-azotetrazole is precipitated with a very acidic solution of bismuth(III) oxide perchlorate (in the improved version, with a less acidic solution of bismuth(III) oxide perchlorate, where only one-third amount of perchloric acid was used). Both methods were two-stage and they required multiple decantation in order to reduce the content of undesirable perchlorates. In both cases, the precipitation began in a neutral medium (the solution of disodium salt of 5,5'-azotetrazole is neutral), and the reaction according to the first method finished in a strongly acidic medium, which caused considerable losses, whereas the reaction according to the "improved" version ended in the range of pH 2-3, which, on one hand, resulted in an increased yield but, on the other, also in a higher pollution with inert hydrolysates of Bi and, thus, impartment of explosiveness of the product.

Thus, the subject matter of the invention is the method of producing ecological explosive—basic bismuth(III) salt of 5,5'-bis-azotetrazole, to primer compositions for ammunition, comprising the following steps:

a) preparation of 0.01 to 0.1 M solution of bismuth(III) alkane sulphonate in distilled/demineralized water;
b) adjustment of pH of the prepared solution to a value around pH=2.5 by titration with 1-5 N solution of hydroxide of alkali metal;
c) heating of thus treated solution to the boiling temperature with subsequent precipitation with 3-5% by weight of aqueous solution of 5,5'-azotetrazolate of alkali metal, relative to weight of azotetrazolate, under intensive stirring;
d) heating of the formed suspension at the boiling temperature for at least 3 min;
e) leaving the suspension containing the precipitate to cool down to room temperature under stirring for a necessary period of time and then allowing it to stand overnight;
f) subsequent filtration of the suspension through a filter, washing of the precipitate with distilled/demineralized water, and dehydration with an organic solvent miscible with water;
g) drying of the amorphous deep yellow basic bismuth (III) salt of 5,5'-azotetrazole at room or elevated temperature.

In accordance with the new method according to this invention—the solution of methane sulphonate of Bi (MSBi) is diluted with water so that the concentration of Bi would be within the range of 0.01-0.1 M, preferably within the range of 0.04-0.05 M, pH is adjusted by partial neutralization with 1-5 N solution of hydroxide of alkali metal, preferably with sodium hydroxide (NaOH), to an optimum value around pH=2.5 at which value the final product reaches the highest quality and the best explosive properties. In the titration with hydroxide, an acido-basic indicator with the most marked colour transition within the range of pH 2-2.5, well soluble in water is preferably used; a pH-meter or similar instrument can also be used for indication of pH; after heating thus treated reaction solution to boiling point, the precipitation is preferably carried out with a saturated 3-5% (preferably about 4%) solution of disodium salt of 5,5'-azotetrazole. Subsequently, the suspension is kept boiling for at least 3 minutes. Due to the sodium ions liberated from the disodium salt of azotetrazole during the reaction, pH value of the resulting suspension is increased. With thus selected concentration, which proved to be an optimum (in particular, regarding the amount of consumed reaction water), the final pH value should range between 3 and 3.5.

The suspension containing the precipitate is left (usually for 1.5-4 hours) to cool down under stirring to room temperature (about 20-25° C.) and then to stand overnight.

The resulting, canary-yellow product sediments much more quickly than the products prepared by the perchlorate method; after standing for several hours (see above—depending on volume of the processed suspension), the product can be separated by filtration directly from the mother solution—the multiple and lengthy decantation was cancelled and, thus, the reaction process was further made substantially more efficient and shorter.

It was also found that the decantation could also be counter-productive—in the original method, when pH was gradually increased by additional pouring of decantation water to reach the value of around 5, opacity occurred of other compounds of Bi which were formed by hydrolysis at higher pH (obviously hydroxides); these compounds further contaminated the product.

After suction off on a filter and thorough multiple washing with water and subsequently with an organic solvent, such as methanol, ethanol, acetone or isopropanol, preferably ethanol or acetone, the product is prepared for drying.

The product is dried at room or elevated temperature of max. up to 100° C.

The product prepared by the method according to the invention is amorphous but can be well filtered through usual filtration materials of porosity 1-2 mcr. Its colour is deep yellow and, contrary to the original product prepared by the perchlorate method, it is incomparably more colour-stable when exposed to sunlight. It is not hygroscopic, does not react with atmospheric gases nor with materials used in the ammunition production. It is insoluble in water—even in boiling water (thus, it is stable against hydrolysis), nor does it dissolve in known organic solvents. It is extremely resistant against action of weak acids and diluted solutions of strong acids. In concentrated mineral acids, it decomposes with formation of corresponding salt of Bi and azotetrazole which, after certain period of time, completely decomposes (this is demonstrated by decolouration of the solution). It reacts with solutions of bases with formation of deep yellow solution of particular alkalic/ammonium salt of azotetrazole and precipitation of white bismuth(III) hydroxide. It is sufficiently heat-stable—in the DTA test, 10 mg detonates when heated at the rate of 5° C./min within the temperature range of 170-180° C. As a performance, it is naturally a weaker explosive than LeadTNR—this generally applies to all basic salts, having higher content of metal than so. called "normal salts" (as LeadTNR). The sensitivity to friction and impact is lower than that of LeadTNR—however, sensitivity to stab ignition in a primer cap is so high that active sensitizers, such as tetrazene (GNGT), need not be used. The sensitivity to electrostatic discharge is lower than in the case LeadTNR, so that antistatic treatment is not necessary.

The product was tested at the Department of Inorganic Chemistry of UCT Praha and was subjected to elemental analysis and Raman spectroscopy; content of Bi was determined by titration and the product was investigated by electron microscopy. This complex analysis proved expected molecular structure of this new product. Its microcrystals have quite regular and compact shape, which facilitates its volumetric dosage.

As the compound formed according to the invention has a lower power than LeadTNR, the ignition mixture had to be supplemented with another energetic compound (powerful component) which is, on its own, described in the literature but its practical usage in the explosives or ammunition industries is also unknown. As it is not commercially available it was necessary to produce it for this purpose as well.

This is preferably 5,5'-bis-tetrazolylhydrazine (hereinafter BTH) which, with its properties, appropriately supplements BBA (basic Bi salts of 5,5-azotetrazole) according to the invention.

5,5'-bis-tetrazolylhydrazine (BTH) is a white, fine crystalline product characterized by high chemical and thermal stabilities. It is not hygroscopic, does not react with atmospheric gases nor with components used in the ammunition production. It is a safe explosive from the handling and storage, in its performance and brisance it is comparable with hexogene.

Both compounds optimally supplement each other—the new initiating explosive-basic Bi salt of 5,5-azotetrazole (BBA) providing high sensitivity to stab ignition and excellent heat transfer by condensing vapours of Bi (of temperature above cca 1600° C.), and BTH with 84% of nitrogen provide the mixture with necessary power in the form of large volume of overheated gases.

The ignition ecological mixture is then preferably supplemented with common inert senzibilizers (e.g. ground glass) and a suitable pyrotechnic system where potassium nitrate or oxides of Bi were used as an oxidizer and amorphous B or some highly calorific powdered metals, such as Ti, Zr, as a fuel. The combination of powdered Al with $KNO_3$ can only be used in the case the "dry technology" of the composition laboration is applied. Due to the amorphous character of the product, it is in this case necessary to apply the method of wet granulation of the composition (commonly well known to experts in the field) in order to achieve maximum volume dosing ability. The resulting granulate can be dry-dosed, however, in the phase of granulation with water, undesirable chemical degradation of the oxidizer with elemental hydrogen, liberated by reaction of powdered Al with water, and subsequent degradation of the composition could take place.

EXAMPLES OF EMBODIMENT

Example 1

The method of producing basic Bi salt of 5,5'-bis-azotetrazole (BBA)—according to the invention:

The vessel of volume 150 l provided with a high-speed propeller stirrer, equipped with jacket for heating and cooling, and two graduated flasks for dosing solutions, a thermometer, and a pH meter—is charged with 4.2 litre of 1 M solution of methane sulphonate of Bi and the solution is diluted with distilled water to volume 80-90 l. Under constant stirring, 0.1% aqueous solution of the indicator (Methanil yellow—Acid yellow 36) is drop-wise added until the solution has a markedly wine colour, and the mixture is titrated with 2-4 N NaOH to deep yellow colour (this corresponds to pH 2.5—check with indicator+possibly pH-meter). The resulting solution is heated to boil and, under intensive stirring, precipitation is carried out with 15 litres of 4% solution of sodium 5,5-azotetrazolate. After the precipitation is completed, the reaction suspension is boiled for additional about 5 minutes, heating is stopped, and the stirred suspension is cooled down to room temperature within additional 2-3 hours. The product is allowed to settle freely and the settled-down product is left standing overnight. Final pH of the mother solution should be within the range of 3-3.5. The suspension is sucked off on a filter (the filtration paper should have max. pore diameter 1-2 mcr), thoroughly washed with distilled water, and subsequently dehydrated with an organic solvent miscible with water (alcohol or acetone); after suction-off, the product is dried at room or elevated temperature of up to 100° C. Subsequently, the product—basic Bi salt of 5,5'-bis-azotetrazole, is prepared for using.

Example 2

For constituting the composition (ignition ecological mixture) for central fire ammunition, the ecological initiating explosive—BBA produced according to example 1—was mixed with BTH, a pyrotechnical system (namely the oxidizer—potassium nitrate ($KNO_3$) and the fuel—boron (B) in the weight ratio 75/25) and frictionator—ground glass with weight percentage as stated below, by commonly known procedures, such as mixing, granulation, drying.

Percentage of the components according to the invention: for central fire ammunition.

| BBA | 40% by weight |
| BTH | 30% by weight |
| BK (KNO3 + B – 75/25) | 20% by weight |
| Ground glass | 10% by weight |

Example 3

Similarly, for constituting the composition (ignition ecological mixture) for rim fire ammunition, the ecological initiating explosive—BBA produced according to example 1—was mixed with BTH, the pyrotechnical system identical with example 2, and the frictionator—ground glass in weight percentage, as stated below, by commonly known procedures, such as mixing, granulation, drying.

Percentage of the components according to the invention: for rim fire ammunition

| BBA | 40% by weight |
| BTH | 20% by weight |
| BK | 20% by weight |
| Ground glass | 20% by weight |

The formed compositions (ignition ecological mixtures) according to example 2 and example 3 were than tested in a primer cup 4.4 SP and 5.3 in stab sensitivity test apparatus and in 9 mm Luger and 5.56×45 cartridges; both ballistic and functional tests were than carried out. The tests unambiguously proved that the ammunition fitted with these primers were fully comparable with the ammunition provided with primers based on a composition of the type NEROXIN.

The composition also showed satisfactory sensitivity in rim fire cartridges 22.LR.

INDUSTRIAL APPLICABILITY

New ecological primary explosive according to the invention will be applicable in all types of ignition compositions for primers for ammunition—both in central and rim fire ammunition where it will fully replace lead trinitroresorcinate. Thanks to highly stable burning, it will also find application in electric fuses and squibs.

In relation to ecology, the initiating explosive itself or wastes from the method of its production have no loading effect whatsoever on the environment due to the fact that both the starting compounds and the products are environmentally friendly and the main resulting product—basic bismuth(III) salt of 5,5'-bis-azotetrazole (BBA), is moreover insoluble in water (even boiling),diluted acids and all known organic solvents!

The starting methane sulphonic acid is a natural component and a part of the eco-system. Thanks to all extreme positive physico-chemical properties in relation to the environment, this acid is called "green acid".

The invention claimed is:
1. Method for producing ecological explosive—basic bismuth(III) salt of 5,5'-bis-azotetrazole, for primer compositions of ammunition, characterized in that it comprises the following steps:
   a. preparation of 0.01 to 0.1 M solution of bismuth (III) alkane sulphonate in distilled/demineralized water;

b. adjustment of pH of the prepared solution to a value around pH=2.5 by titration with 1-5 N solution of hydroxide of alkali metal;
c. heating of thus treated solution to the boiling temperature followed by precipitation with 3-5% by weight of aqueous solution of 5,5'-azotetrazolate of alkali metal, relative to weight of azotetrazolate, under intensive stirring;
d. heating of the formed suspension at the boiling temperature for at least 3 min;
e. leaving the suspension containing the precipitate to cool down to room temperature under stirring for a necessary period of time and then leaving it to stand overnight;
f. filtration of the suspension through a filter, washing of the precipitate with distilled/demineralized water, and dehydration with an organic solvent miscible with water;
g. drying of the amorphous deep yellow basic bismuth (III) salt of 5,5'-bis-azotetrazole at room or elevated temperature.

2. Method for producing ecological explosive according to claim 1, characterized in that bismuth (III) alkane sulphonate is bismuth (III) methane sulphonate.

3. Method for producing ecological explosive according to claim 1, characterized in that the hydroxide of alkali metal is sodium hydroxide.

4. Method for producing ecological explosive according to claim 1, characterized in that 5,5'-azotetrazolate of alkali metal is sodium 5,5-bis-azotetrazolate.

* * * * *